Figure 1:
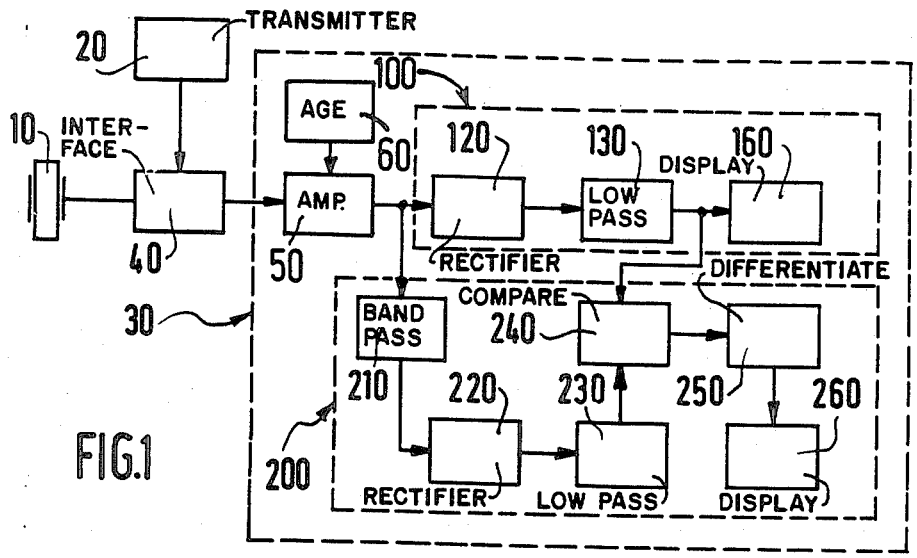

United States Patent [19]

Nicolas et al.

[11] Patent Number: 4,702,258
[45] Date of Patent: Oct. 27, 1987

[54] DEVICE FOR COMBINED B-SCAN AND B/A IMAGING

[75] Inventors: Jean-Marie Nicolas, Paris; Patrick Pesque, Perigny, both of France

[73] Assignee: U.S. Philips Corporation, New York, N.Y.

[21] Appl. No.: 825,844

[22] Filed: Feb. 4, 1986

[30] Foreign Application Priority Data

Feb. 8, 1985 [FR] France ................... 85 01790

[51] Int. Cl.$^4$ ............................................. A61B 10/00
[52] U.S. Cl. ................................................... 128/660
[58] Field of Search ........................... 128/660; 73/597

[56] References Cited

U.S. PATENT DOCUMENTS 4,566,460  1/1986  Sato et al. ............................ 128/660
4,605,008  8/1986  Ferrori .................................. 128/660
4,610,255  9/1986  Shimura et al. ...................... 128/660

OTHER PUBLICATIONS

Sanders, R. C. et al., "Ultrasound Annual–Ultrasonic Tissue Characterization" Raven Press, N.Y. 1985 pp. 122, 125–127.

Primary Examiner—William E. Kamm
Assistant Examiner—Francis J. Jaworski
Attorney, Agent, or Firm—Jack E. Haken

[57] ABSTRACT

The combined modality device comprises an ultrasound transducer (10) which is suitable for transmission as well as reception and which is connected to a transmitter stage (20) as well as to a receiver stage (30). The transducer (10) has a bandwidth which at least equals approximately one octave. The transmitter stage (20) comprises a generator for generating activation signals for the transducer (10) with a frequency $f_o$ near the lower limit of said bandwidth, the spectrum of these activation signals excluding the frequency $f_1 = 2f_o$. The receiver stage (30) comprises a B-scan channel and also a B/A processing channel (200) which itself includes a bandpass filter (210) which is centered around said frequency $f_1$, an envelope detector (220, 230), a comparison circuit (240), a differentiation circuit (250) and a display device (260) whereby measured results in both modalities may be displayed.

4 Claims, 2 Drawing Figures

DEVICE FOR COMBINED B-SCAN AND B/A IMAGING

The invention relates to a device for the examination of objects, notably biological tissues, by means of ultrasound echography, comprising an ultrasound transducer which is suitable for transmission as well as reception and which is connected to a transmitter stage for the repeated transmission of ultrasound signals and also to a receiver stage for the reception and processing of the ultrasound echoes which correspond to the obstacles encountered by the transmitted signals in their propagation direction, which receiver stage comprises a processing circuit for the echoes received which is composed of an amplifier and gain control circuit and a first processing channel which itself comprises a first envelope detector and a first display device.

This device can be used notably in the medical field for the echographic examination of biological tissues, but can also be used for the non-destructive testing of materials.

A device of the kind set forth is described in French Patent Application No. 2514910. The known device serves to collect quantitative information as regards the variations of the differential ultrasound attenuation coefficient in the objects examined, said information being obtained by calculation of a local parameter which is directly related to the value of said coefficient.

It is an object of the invention to provide a device of the kind set forth which enables quantitative information concerning the nature of the objects examined to be obtained in a different manner, that is to say by determination of the parameter of the acoustic second order non-linearity of these objects, said parameter also being referred to as B/A parameter in which A and B are the linear and the quadratic coefficient, respectively, of the formula expressing the relationship between the variations of the pressure and the variations of the specific mass of the objects examined.

To achieve this, the device in accordance with the invention is characterized in that the transducer has a bandwidth which at least equals approximately one octave, the transmitter stage comprising a generator for generating activation signals for the transducer having a frequency $f_o$ in the vicinity of the lower limit of said bandwidth, the spectrum of these activation signals excluding the frequency $f_1 = 2f_o$, the receiving and processing stage comprising a second processing channel which itself includes a bandpass filter having a central frequency which is equal to said frequency $f_1$, a second envelope detector, a comparison circuit for comparing the output signals of the detectors, a differentiation circuit, and a second display device.

Figure 2:
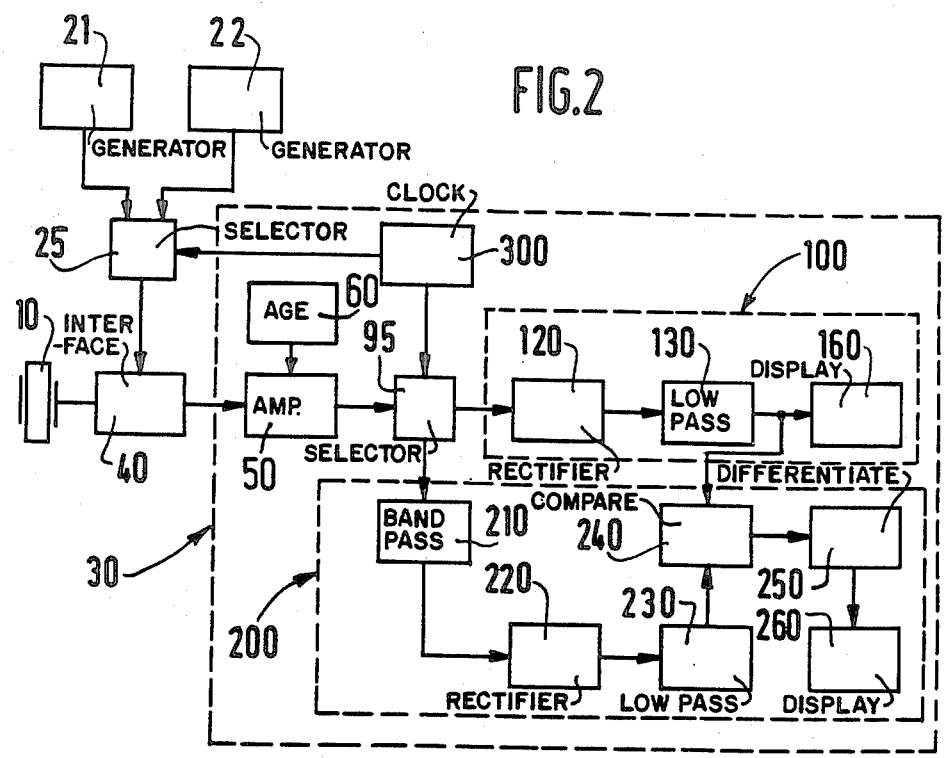

The invention will be described in detail hereinafter by way of example with reference to the drawings: therein, FIGS. 1 and 2 show two embodiments of the device in accordance with the invention.

The embodiment of the device described with reference to FIG. 1 comprises an ultrasound transducer 10 which is suitable for transmission as well as reception and which is connected to a transmitter stage 20 for the repeated transmission (in this case periodically) of ultrasound waves to the object to be examined, as well as to a receiving and processing stage 30. The transducer 10 is in this case formed by a piezo-electric transducer which includes matching layers and a ceramic element which resonates at a frequency $f_R$ near the frequency $3f_o/2$, in which $f_0$ is the frequency of the signal transmitted by the stage 20. The matching layers are constructed so that the energy yield of the transducer 10 is satisfactory at the frequency $f_0$ as well as at the frequency $f_1 = 2f_o$, so that its bandwidth at least equals this frequency band $f_o$ to $f_1$. For example, use is made of two $\lambda/4$ matching layers having an impedance of from 7 to 11 MRayls and from 2 to 5 MRayls, respectively, which matching layers are connected to a piezo-electric material of the PZT-type having an impedance of approximately 30 MRayls as well as to a light absorbing backing layer having an impedance of from 0 to approximately 3 MRayls.

The transmitter stage 20 transmits ultrasound wave in known manner, be it that the spectrum of the transmitted signal may not include the frequency $f_1 = 2f_o$; to this end, this stage can notably be provided with a band-rejection filter having a narrow bandwidth which is centered around said frequency $2f_o$. The receiving and processing stage 30 first of all includes an amplifier 50 which receives the electric signals from the transducer 10 which correspond to the ultrasound echoes received by the transducer. The amplifier is connected to an automatic gain control circuit 60 which increases the gain of the amplifier as a function of time in order to compensate for the increasing attenuation effect of the ultrasound waves during propagation. Between the transducer 10 and the stages 20 and 30 there may be provided an interface circuit 40 in order to connect one of the two stages selectively to the transducer, this avoiding overdriving of the receiver stage by the transmitter stage.

To the output of the amplifier 50 of the receiving and processing stage 30 there are connected two parallel processing channels 100 and 200; the first procedding channel 100 is of a conventional type and successively includes an envelope detector which is composed of a first rectifier 120 and a first lowpass filter 130, and a first display device 160 while the second channel 200 successively includes a bandpass filter 210 which is centered around the frequency $f_1$, a second rectifier 220, a second lowpass filter 230, a comparison circuit 240 for the output signals of the lowpass filters 130 and 230, a differentiating circuit 250, and a second display device 260. It will be apparent that the two display devices 160 and 260 can be replaced by one display device provided with two separate screens which can be independently or simultaneously controlled in all cases.

The second processing channel 200 serves to provide access to an image representing the variation of the acoustic secondorder non-linearity parameter, the so-called B/A parameter. This is because during the examination of the object the transmitted series of waves produces in any point a wave having a twice as high frequency in the same direction, said wave being dependent on the value of the B/A coefficient at the relevant point. Because biological tissues are assumed to be non-dispersive, the propagation speed of the waves having a twice as high frequency will be the same as the propagation speed of the initial wave series. Consequently, the echographic signal obtained from the waves having a twice as high frequency can be compared with the original echographic signal by means of the comparison circuit 240. The result of this comparison which is followed by a differentiation for determining the local parameter, this represents the variation of the B/A parameter. The images from the first (conventional)

channel 100 and the second channel 200 are A-type echograms in the present case (reproduction of amplitudes in the ordinates as a function of time in the abscissa), but the transducer 10 may alternatively be displaceable so that B-type echograms can be obtained.

FIG. 2 shows a second embodiment in accordance with the invention in which elements which correspond to elements of the first embodiment shown in FIG. 1 are denoted by corresponding reference numerals. The transmitter stage comprises a selection circuit for the transmission signals 25, two generators 21, 22 being connected parallel to the inputs of said selection circuit. The first generator 21 is a conventional type for generating activation signals for the transducer, said signals being as short as possible in order to improve the resolution in the axial direction. The second generator 22 is especially intended for the measurement of the B/A parameter and supplies activation signals which consist of a plurality of sine-wave periods having the frequency $f_o$. Between the amplifier and gain control circuit 50, 60 and the processing channels 100 and 200 in the receiving stage there is connected a processing selection circuit 95, the two processing channels being connected in parallel to the outputs thereof. The selection circuits 25 and 95 are simultaneously controlled by a clock circuit 300 in order to synchronize the selection of either the generator 21 and the first channel 100 or the generator 22 and the second channel 200.

It will be apparent that the invention is not restricted to the described embodiments; within the scope of the invention, various alternatives exist. It is to be noted, for example that when use is made of a display device comprising two display screens, both screens can be controlled either independently or simultaneously. Use can also be made of a display device which comprises one screen on which colour images are displayed and which is controlled as regards luminance by the output signal of the first processing channel 100 and as regards chrominance by the output signal of the second channel 200.

What is claimed is:

1. A device for the production of both conventional and B/A second order non-linearity images of objects, notably biological tissues, by ultrasound echography comprising:
   an ultrasound transducer;
   transmitter means connected to the transducer to produce repeated transmission of pulses of ultrasound energy;
   receiver means connected to the transducer for receiving signals which correspond to echoes of the pulses of ultrasound energy which are received by the transducer, said receiver means comprising:
   an amplifier, with automatic gain control, connected to receive and amplify signals from the transducer;
   a first processing channel for producing conventional images, having an input connected to the output of the amplifier and comprising, in functional cascade connection, a first envelope detector and first display means; and
   a second processing channel for producing B/A second order non-linearity images, having an input connected to the output of the amplifier and comprising, in functional cascade connection, a bandpass filter, a second envelope detector, comparison means which compare the output of the first envelope detector with the output of the second envelope detector, differentiation means, and second display means;
   wherein the transducer has a bandwidth which is approximately equal to or greater than one octave, the transmitter means comprise means for generating transducer activation signals having the nominal frequency $f_0$ in the vicinity of the lower limit of the bandwidth of the transducer, the spectrum of the activation signals excludes a frequency $f_1 = 2f_0$, and the bandpass filter has a central frequency equal to said frequency $f_1$.

2. A device as claimed in claim 1 wherein the first display means and the second display means comprise separate display screens.

3. A device as claimed in claim 1 wherein:
   the transmitter means comprise: first generator means for generating short activation signals for the transducer which are used for the production of conventional images, second generator means for a generation of activation signals which are used for the production of B/A images and which consist of a plurality of sine wave periods having a nominal frequency $f_0$, and first selection means which selectively apply either the signals from the first generator means or the signals from the second generator means to the transducer;
   the receiver means comprise second selection means which selectively direct the output of the amplifier to either the first channel or the second channel; and
   the selection circuits being simultaneously controlled to synchronize selection of the generator means with application of received signals to a corresponding one of said channels.

4. A device as claimed in claim 1 or 3 comprising a color display device, said first display means control the luminescence of an image on said device and said second display means control the chrominance of the image on said device.

* * * * *